United States Patent [19]
Larkins et al.

[11] Patent Number: 5,641,892
[45] Date of Patent: Jun. 24, 1997

[54] INTRAVENOUS-LINE AIR-DETECTION SYSTEM

[75] Inventors: William T. Larkins; Russell Beavis, both of Manchester; Dean L. Kamen, Bedford, all of N.H.

[73] Assignee: DEKA Products Limited Partnership, Manchester, N.H.

[21] Appl. No.: 477,380

[22] Filed: Jun. 7, 1995

[51] Int. Cl.$^6$ .................... G01N 29/00; G01N 29/02
[52] U.S. Cl. ............................ 73/19.03; 73/149
[58] Field of Search ................... 73/19.03, 149, 73/290 B, 290 V, 61.75

[56] References Cited

U.S. PATENT DOCUMENTS

| | | | |
|---|---|---|---|
| 3,075,382 | 1/1963 | Mathias | 73/149 |
| 3,596,510 | 8/1971 | Siegel et al. | 73/149 |
| 4,926,675 | 5/1990 | Schohl et al. | 73/19 |
| 5,026,348 | 6/1991 | Venegas | 604/122 |
| 5,349,852 | 9/1994 | Kamen et al. | 73/149 |

Primary Examiner—Hezron E. Williams
Assistant Examiner—Jay L. Politzer
Attorney, Agent, or Firm—Bromberg & Sunstein LLP

[57] ABSTRACT

The flow of an intravenous (IV) fluid from a IV source through an IV line to a patient is controlled, while monitoring whether there is any bubble in the liquid being delivered to the patient. Disposed in the line is a region having a first portion containing a measurement gas and a second portion containing a segment of the liquid flowing through the line. The liquid in this region is tested for the presence of an air bubble. The sum of the first portion's volume and the second portion's volume should be a constant volume. The region is part of an acoustically resonant system, in the volume of the measurement gas in the first portion of the region can be determined from the resonant frequency. Preferably, the acoustically resonant system is tuned so as to prevent the presence of a bubble from significantly affecting the measurement of the volume of the region's first portion. The region should be isolatable from pressure effects in the rest of the line, preferably by means of a first valve that controls flow from the source and a second valve that controls flow to the patient. The resonant system includes at least one speaker and one microphone, arranged so that the resonant frequency of the system can be detected. In addition, some means for changing the pressure of the measurement gas in the resonant system is provided.

20 Claims, 5 Drawing Sheets

INTRAVENOUS-LINE AIR-DETECTION SYSTEM

DESCRIPTION

Related Applications

This application describes an improvement of the technology disclosed in U.S. Pat. No. 5,349,852, for an invention by Kamen, Seale, Briggs and Arnold. Filed concurrently herewith are applications Ser. No. 08/478,065, entitled "Cassette for Intravenous-Line Flow-Control System" for an invention by Houle and Larkins, Ser. No. 08/472,212, entitled "Intravenous-Line Flow-Control System" for an invention by Heinzmann, Kamen, Lanigan, Larkins, Lund and Manning, and Ser. No. 08/481,606, entitled "Intravenous-Line Air-Elimination System" for an invention by Manning, Larkins, Houle, Kamen and Faust. All of these applications and the foregoing patent are incorporated herein by reference.

Technical Field

The present invention relates to apparatus and methods for detecting air bubbles in intravenous lines, and in particular to apparatus and methods for measuring and controlling flow through an intravenous line while also detecting air bubbles.

Summary of the Invention

In a preferred embodiment, the invention controls the flow of an intravenous (IV) fluid from a IV source through an IV line to a patient, while monitoring whether there is any bubble in the liquid being delivered to the patient. Disposed in the line is a region having a first portion containing a measurement gas and a second portion containing a segment of the liquid flowing through the line. The liquid in this region is tested for the presence of an air bubble. The sum of the first portion's volume and the second portion's volume should be a constant volume. The region is part of an acoustically resonant system, and the volume of the measurement gas in the first portion of the region can be determined from a resonant frequency of the acoustic system. Preferably, the acoustically resonant system is tuned so as to prevent the presence of a bubble from significantly affecting the measurement of the volume of the region's first portion. The region should be isolatable from pressure effects in the rest of the line, preferably by means of a first valve that controls flow from the source and a second valve that controls flow to the patient. The resonant system includes at least one speaker and one microphone, arranged so that the resonant frequency of the system can be detected. In addition, some means for changing the pressure of the measurement gas in the resonant system is provided. A controller is also provided for controlling the valves, the resonance-detection means, and the pressure-changing means, and for generating a signal indicating the presence of a bubble. Preferably, the controller also includes means for determining the volume of the measurement gas in the region's first portion based on a measured resonant frequency.

The invention is preferably used in the following manner in order to determine whether a bubble is present in the liquid in the second portion of the region. First, the resonant frequency of the system is determined while the measurement gas is at a first pressure. The volume of the region's first portion at this pressure may be determined based on the resonant frequency at the first pressure. Then, the pressure of the measurement gas is changed to a second pressure, and the resonant frequency of the system at this second pressure is measured. Similarly, the first portion's volume at the second pressure may be determined based on the resonant frequency at the second pressure. If a bubble is present in the liquid, the bubble will be compressed if the pressure is increased, or will expand if the pressure is reduced. Thus, the presence of a bubble can be detected by a change in the volume occupied by the measurement gas in the first region, and thereby a change in the volume occupied by the liquid and the bubble in the region's second portion. If there is a bubble present in the liquid, the liquid may be purged from the region back to the fluid source. If there is no bubble present in the liquid, the liquid may be pumped to the patient. The measured resonant frequencies may be used to determine the volume of liquid in the region before and after a portion of it has been administered to a patient, the difference in volumes being the amount delivered to the patient.

DETAILED DESCRIPTION OF SPECIFIC EMBODIMENTS

Figure 1:
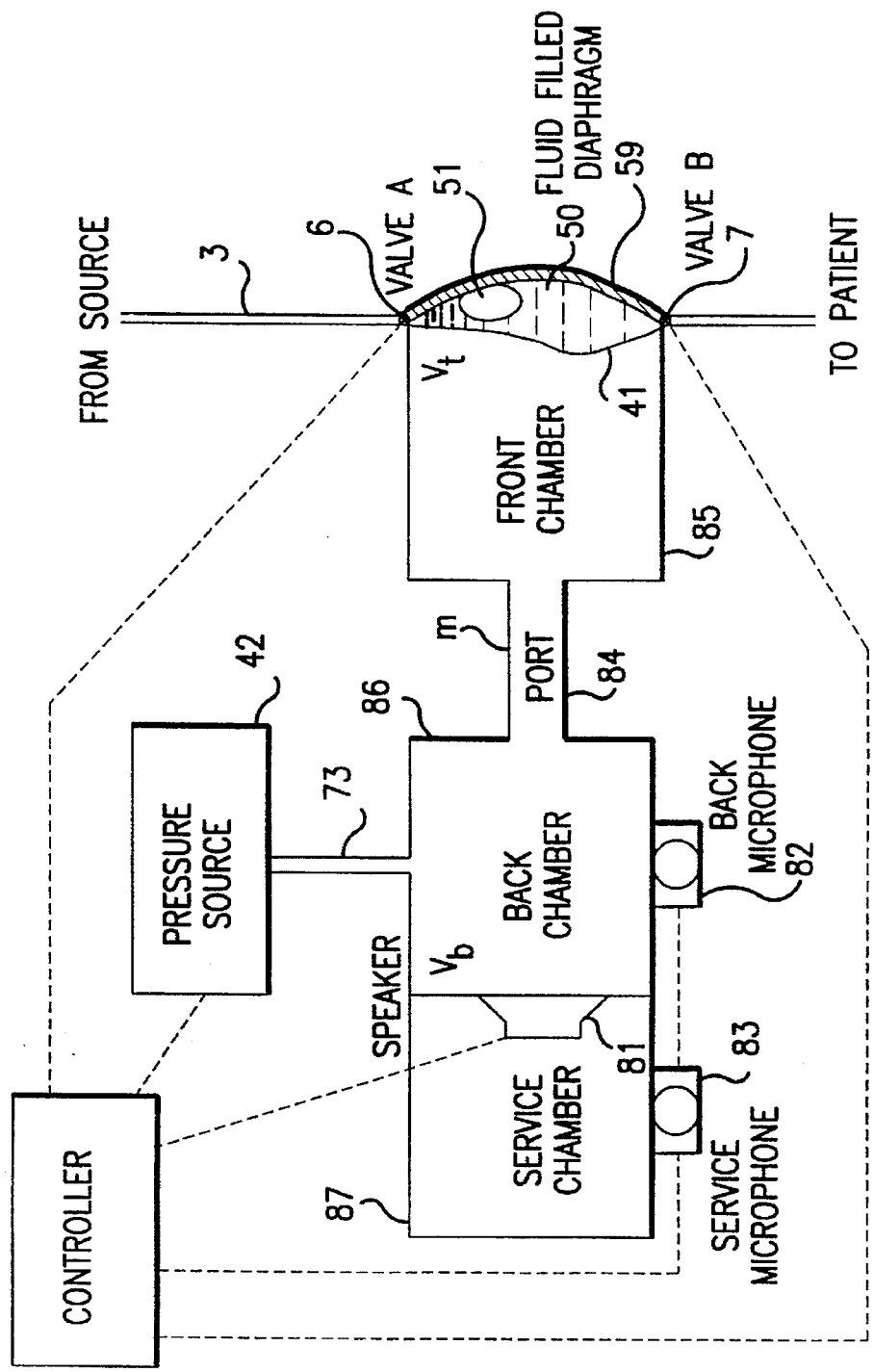
FIG. 1 shows a schematic of the mechanical arrangement of an acoustically resonant system that may be used in the present invention.

FIG. 1 depicts an acoustically resonant system that may be used for determining the volume ($V_f$) of the front chamber 85 that is occupied by a measurement gas, preferably air. The volume of the front chamber 85 varies with the amount of IV fluid in an isolatable region 50 of the IV line 3, located between valves 6 and 7. The sum of the volume of the IV fluid in the region (including any bubble 51) and the volume ($V_f$) of measurement gas in the front chamber 85 is constant, so that if the volume ($V_f$) of the measurement gas in the front chamber 85 and the total volume are known, the volume of IV fluid in the region 50 between the valves 6 and 7 can easily be determined by simply subtracting the measurement gas volume ($V_f$) from the total volume. In order to measure the flow rate through the IV line, however, one need only measure how much the measurement gas volume ($V_f$) has changed in order to determine how much IV fluid has been dispensed to the patient. A membrane 41 separates the IV fluid from the front chamber 85. Preferably, all portions of the apparatus that come into contact with the IV fluid— which in the depicted embodiment are the IV line 3, the valves 6 and 7, the membrane 41, and a rigid wall 59 (that together with the membrane 41 and the valves 6 and 7 define the boundaries of the isolatable region 50 of the IV fluid) —are disposable. The remainder of the apparatus is kept from coming into direct contact with the IV fluid.

The front chamber 85 is connected to a back chamber 86 by a port 84. The port 84 contains a mass (m) of measurement gas that can resonate. A speaker 81, preferably of the piezo-crystal type although any suitable electro-acoustical transducer may be used, to introduce acoustic energy at various frequencies into the system. The speaker 81 forms part of a wall that separates the back chamber 86 from a service chamber 87. Microphones 82 and 83, preferably of the electret type although any suitable acousto-electrical transducer may be used, are placed in each of the back chamber 86 and a service chamber 87. The back chamber's microphones 82 is used to detect the response of the system to the acoustic energy created by the speaker 81, and the response detected by the service chamber's microphone 83 is used to calibrate continuously the speaker 81 and the back chamber's microphone 82.

Connected to the back chamber 86 is a pressure source 42, which provides measurement gas to the back chamber 86 and/or draws measurement gas out of the back chamber 86, so as to change the pressure exerted on the membrane 41 by the measurement gas. The pressure source 42 may comprise a piston, a pump, or supplies of positive and/or negative pressure. The pressure source 42 is connected to the system by a long, thin tube 73, so as to prevent the pressure source 42 from affecting the acoustical parameters of the system. The pressure source 42 can work as a pump on the IV fluid, by decreasing the pressure on membrane 41 when valve 6 is open so as to draw IV fluid into the isolatable region 50 from the IV source, and by causing an increase in pressure against the membrane 41 when valve 7 is opened so as to force IV fluid to the patient. A controller, preferably similar to the controller discussed in connection with FIGS. 12 and 13 of the above-referenced U.S. Pat. No. 5,349,852, controls the valves 6 and 7, and the pressure source 42, and causes the speaker 81 to vibrate at given frequencies, while interpreting the responses from the microphones 82 and 83.

Figure 2:
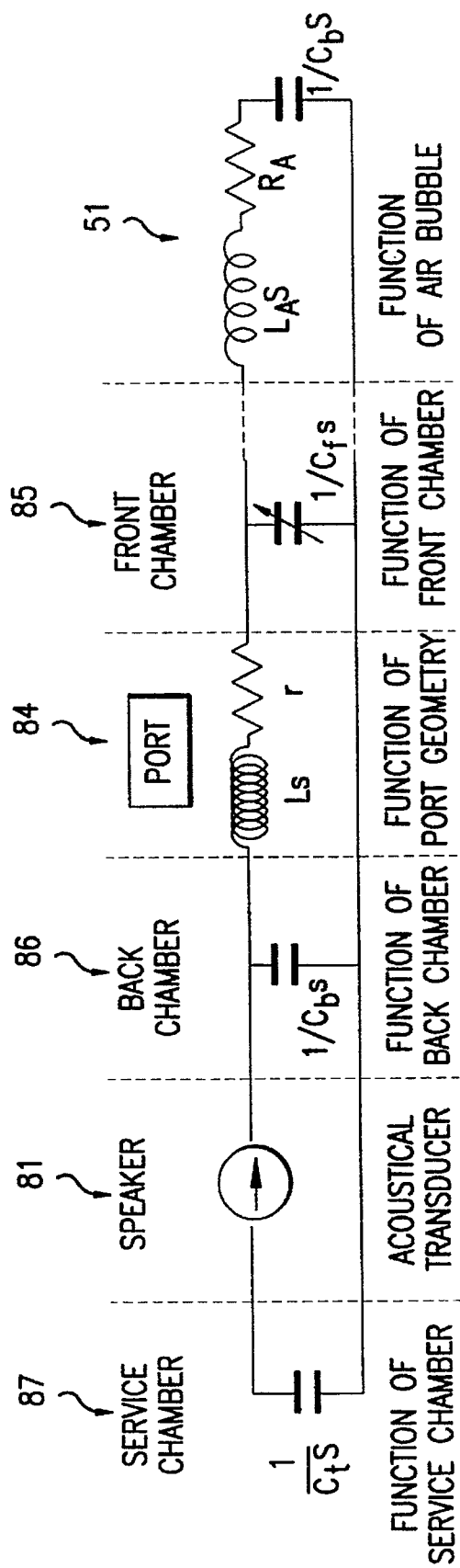
FIG. 2 is an electrical model of the resonant system shown in FIG. 1.

FIG. 2 shows an electrical model of the acoustically resonant system shown in FIG. 1. As shown in the FIG. 2 model, the "capacitance" of the front chamber 85 varies, since the volume ($V_f$) of the front chamber varies. As also shown in the FIG. 2 model, the presence of a bubble 51 in region 50 can create an additional resonant frequency. The effect of the bubble varies with the size of the bubble: generally, the larger the bubble the lower the resonant frequency created by the bubble and the greater the amplitude of the peak acoustic response at that resonant frequency. The response of smaller bubbles will generally have smaller peak amplitudes and will have higher resonant frequencies.

In the preferred embodiment of the invention, the sizes of the port 84, the front chamber 85 and the back chamber 86 are preferably configured—that is, the system is tuned—so that large bubbles do not have a substantial effect on the volume measurement. By tuning the system high enough— that is, by making the inductance of the port 84 relatively low—the system can be excited by the speaker 81 at a relatively high resonant frequency while the relatively high inductance of a bubble 51 (or more precisely the bubble's coupling to the rest of the system, i.e., the IV fluid and membrane material between the bubble and the measurement gas in the front chamber) will render the bubble imperceptible to the microphone 82. (By way of illustration in the electrical model of FIG. 2, the bubble's relatively high inductance ($L_A$) with respect to the port's inductance (L) causes an "open circuit" at high frequencies between the model's components for the bubble and the model's component for the front chamber, so that the function of the bubble does not affect the function of the rest of the acoustic system.) In tuning the port 84 high enough to minimize the effect of large air bubbles, it is important that it is tuned low enough so that the acoustic system behaves more as a lump model (as depicted in the FIG. 2 electrical model) than a distributive model.

In the electrical model shown in FIG. 2, the inductance L of the port 84 corresponds to the physical system as follows:

$$L = \frac{\rho m l_e}{A} \quad (1)$$

where the effective length of the port ($l_e$) equals the sum of the length of the port and the port's diameter ($l_e = l + 2r$), A is the cross-sectional area of the port, $\rho$ is the gas density in moles/vol, and m is the gas mass density in units of mass/mole. The capacitance C in the model corresponds to the physical system as follows:

$$C = \frac{V}{\gamma R T \rho}, \quad (2)$$

where R is the Boltzmann constant 8.31 Joules/°K-mole), T is absolute temperature, and $\gamma$ is the constant for adiabatic compression for the gas. Since $$\omega_{res} = \frac{1}{\sqrt{LC}}, \quad (3)$$

where $\omega_{res}$ denotes resonant frequency in rad/sec, then $$(2\pi f_{res})^2 = \omega_{res}^2 = \frac{1}{m l_e \frac{\rho}{A} \frac{V}{\gamma R T \rho}}, \quad (4)$$

where $f_{res}$ denotes resonant frequency in Hz, and thus, in a simple system, $$V = \frac{T}{f^2} \frac{A}{l_e} \frac{1}{m} \frac{R\gamma}{(2\pi)^2}, \quad (5)$$

which is equivalent to equation (2) in the above-referenced U.S. Pat. No. 5,349,852.

Performing a Laplacian analysis for the FIG. 1 embodiment as modeled in FIG. 2 in which speaker 81 is modeled as a current source provides the following pair of equations, the first being the transfer function for the electrical network of FIG. 2 which is defined to be the ratio $V_b(S)/V_f(S)$, where $V_b(S)$ and $V_f(S)$ respectively denote the Laplace transforms of the voltages across capacitors $C_b$ and $C_f$ in FIG. 2 (where the direction for determining the sign of $V_b(S)$ is opposite to that of $V_f(S)$), and the second equation being an expression for the phase $\phi$ of the transfer function:

$$\frac{V_b(s)}{V_f(s)} = \frac{C_f}{C_b} \left[ \frac{s^2 + \frac{r}{L} * s + \frac{1}{LC_f}}{s^2 + \frac{r}{L} * s + \frac{1}{LC_f} + \frac{1}{LC_b}} \right] \quad (6)$$

and $$\phi = \arctan \left[ \frac{-\omega\sigma\omega_b^2}{(\omega_f^2 - \omega^2)(\omega_f^2 + \omega_b^2 - \omega^2) + \omega^2\sigma^2} \right] \quad (7)$$

where the effect of $L_A$, and $R_A$, and $C_A$ (see 51 of FIG. 2) has been ignored in computing the transfer function, r is a resistance (see FIG. 2), and the following substitutions were made:

$$\omega_b = \frac{1}{\sqrt{LC_b}},$$

$$\omega_f = \frac{1}{\sqrt{LC_f}},$$

-continued and $$\sigma = \frac{r}{L}.$$

The resonances are located at the points where the denominator equals zero. Therefore, $$\omega^2 = \omega_f^2 + \omega_f^2 \left| \frac{\frac{\omega_b^2}{\omega_f^2} + \frac{1}{Q^2} \pm \sqrt{\left(\frac{\omega_b^2}{\omega_f^2} + \frac{1}{Q^2}\right)^2 + 3 \cdot \frac{1}{Q^2}}}{2} \right|, \quad (8)$$

where the following substitution was made:

$$\sigma = \frac{\omega_f}{Q}.$$

If Q is sufficiently larger than 1, then the above can be reduced to:

$$\omega_1^2 = \omega_f^2 \quad (9)$$

and $$\omega_2^2 = \omega_f^2 + \omega_b^2. \quad (10)$$

Figure 3:
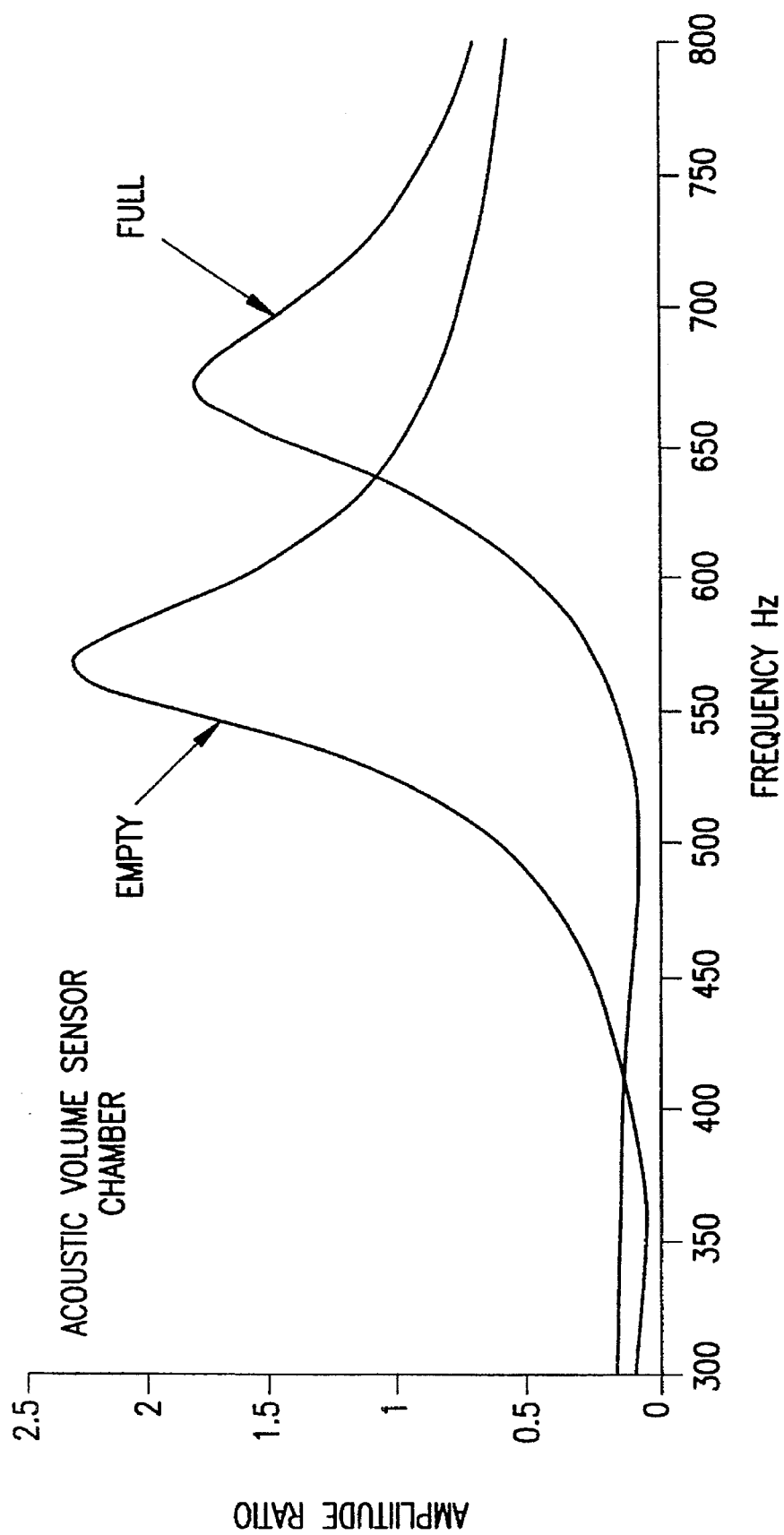
FIG. 3 is a plot of the amplitude of the acoustic response of the FIG. 1 system over a range of input frequencies.
Figure 4:
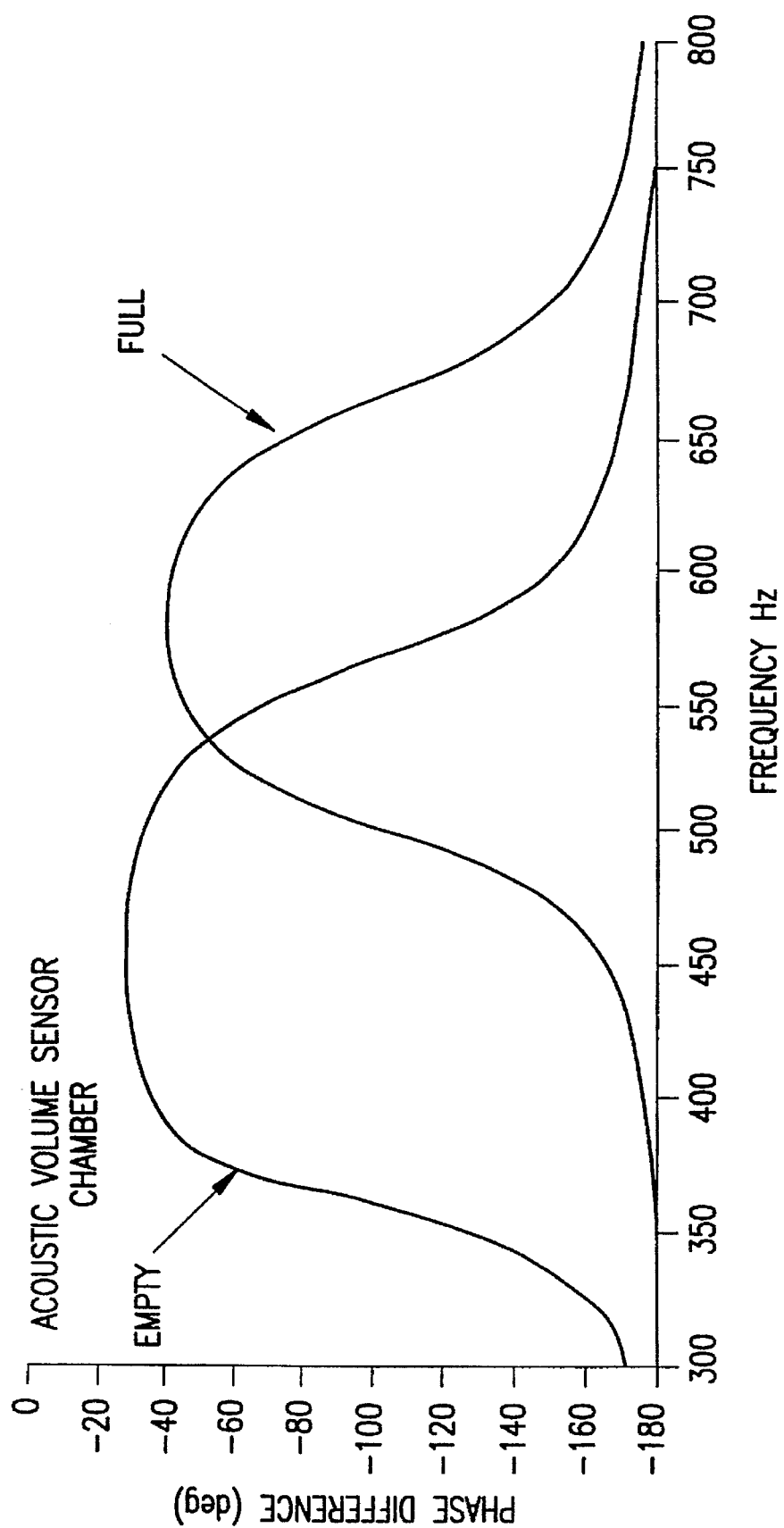
FIG. 4 is a plot of the phase change of the acoustic response of the FIG. 1 system over a range of frequencies.

The volume can then be calculated from the resonances as follows:

$$\omega_f^2 = \frac{K \cdot T}{V_f} \quad (11)$$

$$\omega_b^2 = \frac{K \cdot T}{V_b} \quad (12)$$

$$\frac{\omega_2^2}{\omega_1^2} = \frac{\frac{K \cdot T}{V_f} + \frac{K \cdot T}{V_b}}{\frac{K \cdot T}{V_f}} \quad (13)$$

$$V_f = V_b \left( \frac{\omega_2^2}{\omega_1^2} - 1 \right), \quad (15)$$

where K=(ARγ)/(l_em). Thus, since the volume of the back chamber ($V_b$) is fixed and known, the volume of air ($V_f$) in the front chamber 82 can be determined based on the detected frequencies of resonance ($\omega_2$) and "anti-resonance" ($\omega_1$). FIGS. 3 and 4 show respectively the amplitude and the phase change of the acoustic responses of the acoustic system of FIG. 1 over a range of frequencies from 300 to 800 Hz for when $V_f$ is at a minimum, i.e., when the isolatable region 50 is full, and at a maximum, i.e., when the isolatable region 50 is empty. As can be seen in the amplitude graph of FIG. 3, the system shown in FIG. 1 has a resonant or peak frequency ($\omega_2$) at approximately 560 Hz when the region 50 is empty and 670 Hz when the region is full. An "anti-resonance" or minimum-gain frequency ($\omega_1$) is found at approximately 360 Hz when the region 50 is empty and 510 Hz when the region is full. Both the resonant and anti-resonant frequencies are further indicated on the phase-change graph of FIG. 4 by the points where the phase change equals 90°.

Because the signal-to-noise ratio is low when determining the anti-resonant frequency ($\omega_1$), it is often more accurate and therefore preferable to determine the front chamber's volume ($V_f$) without having to rely on the anti-resonant frequency ($\omega_1$). An alternative method of determining the front chamber's volume ($V_f$) relies on the resonant frequency ($\omega_2$) and the temperature (T), which can be measured by placing a temperature sensor adjacent to the outside of the port, as well as the volume ($V_b$) of the back chamber, which is known. From equations 10-12 above, $$\omega_2^2 = \frac{K \cdot T}{V_f} + \frac{K \cdot T}{V_b} \quad (16)$$

which can be solved for the front chamber's volume as follows:

$$V_f = \frac{K \cdot T}{\omega_2^2 - \frac{K \cdot T}{V_b}} \quad (17)$$

Thus, the volume of the front chamber ($V_f$) can be ascertained from the resonant frequency ($\omega_2$) of the system and the temperature (T). Assuming the temperature remains substantially constant between determinations of resonant frequency, one can determine whether a change occurs in the front chamber's volume by simply determining whether there was a change in the resonant frequency.

In order to detect a bubble, the pressure in the front chamber 85 is changed by means of the pressure source 42. Preferably, the pressure in the front chamber 85 is increased, so that, if no bubble is detected, the additional pressure may be used to force the IV fluid to the patient when the outlet valve 7 is opened. If there is a bubble 51 in the IV fluid, the change in pressure in the front chamber 85 will cause a change in the volume of the IV fluid in the isolatable region 50, and in turn a corresponding opposite change in the volume ($V_f$) of the front chamber 85. Thus, an increase in pressure causes the bubble to decrease in size and thereby causes the volume in the front chamber to increase by the same amount. If there is no bubble in the IV fluid, the volume ($V_f$) of the front chamber will not will not change, since liquid is substantially incompressible at normal pressures. Thus, a change in volume ($V_f$) indicates a bubble, whereas no change in the volume indicates the absence of a bubble. A change in volume ($V_f$) may be determined by calculating the volumes before and after the pressure change in the manners described above—specifically, based on the resonant and anti-resonant frequencies ($\omega_2$ and $\omega_1$) before and after the pressure change, or based on the resonant frequencies ($\omega_2$) and temperatures (T) before and after the pressure change. Alternatively, if the temperature change is insignificant, a change in volume ($V_f$) may be detected simply by determining if there is a change in the resonant frequency. The change in pressure does not substantially affect the detection of resonance and the determination of the front chamber's volume ($V_f$), except to the extent the change in pressure affects the temperature of the measurement gas. (The change in pressure is in some ways analogous to applying a DC voltage component to the electrical model in FIG. 2; it does not affect the resonant frequency.)

In a preferred process of using the apparatus shown in FIG. 1, the outlet valve 7 is initially closed, and inlet valve 6 is opened so as to permit flow from the IV source into the isolatable region. After the region is sufficiently filled and before a pressure change is introduced into the front chamber, the inlet valve 6 is also closed so that the region is isolated from pressure in the rest of the IV line 3. The speaker 81 introduces acoustic energy into the system at varying frequencies until the resonant frequency of the acoustic system is detected. The resonant frequency may be determined in one of the manners described in the above-referenced U.S. Pat. No. 5,349,852, and preferably the manner discussed in connection with FIGS. 13 and 17 of said patent. This resonant frequency may then be used to determine the volume ($V_f$) of the front chamber. The pressure in the front chamber is changed—preferably increased by adding measurement gas from the pressure source 42—while the region 50 of IV fluid is isolated from pressure effects from the rest of the line. The resonant frequency is again determined. The two measured resonant frequencies are analyzed by an electronic controller to determine whether the volume of the front chamber has changed.

If a change in the front chamber's volume ($V_f$) is indicated, then the controller generates a signal indicating the presence of a bubble. Preferably, this signal causes valve 6 to open, while valve 7 remains closed, and then causes the pressure source 42 to increase the pressure against the membrane to cause the IV fluid in the isolatable region 50, including the bubble 51, to be forced back to the IV source. This and other methods for causing the bubble to be returned to the IV source are discussed in greater detail in above-referenced, concurrently filed application Ser. No. 08/481, 606, entitled "Intravenous-Line Air-Elimination System" for an invention by Manning, Larkins, Houle, Kamen and Faust.

Figure 5:
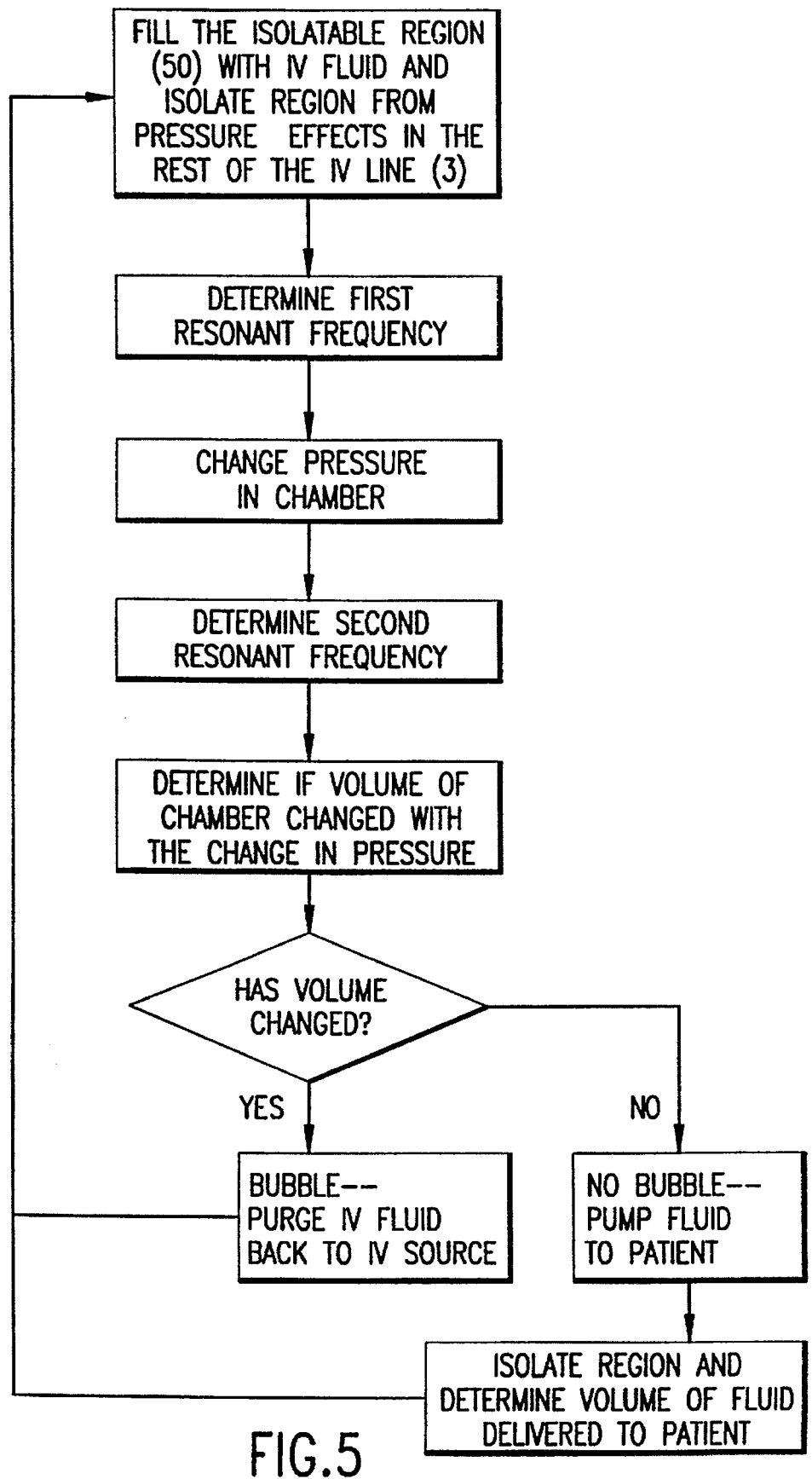
FIG. 5 is a flow chart of a preferred method according to the present invention.

If no change in the front chamber's volume ($V_f$) is indicated, then the controller causes the valve 7 to open, so that IV fluid may be delivered to the patient. The amount that valve 7 (or another valve downstream of the isolatable region) is opened and the amount of pressure applied by the pressure source 42 are controlled so as to control the flow rate of IV fluid to the patient. The change in volume in the front chamber may be tracked by the controller by following the TRACK-mode process described in connection with FIG. 17 of the above-referenced U.S. Pat. No. 5,349,852. When a sufficient amount of IV fluid has ben dispensed, then valve 7 is closed again; at which point, the volume ($V_f$) of the front chamber may again determined. The volume of the front chamber measured before valve 7 was opened may be subtracted from the volume of the front chamber after valve 7 is closed to determine the amount of IV fluid delivered to the patient during that cycle. The cycle may be repeated—starting with the opening of valve 6, then the filling of the isolatable region, the determination of volume, the determination of whether a bubble is present in the IV fluid in the isolatable region, etc.—until the desired amount of IV fluid is delivered to the patient. FIG. 5 is a flowchart showing a preferred method of carrying out the invention. The controller preferably keeps track of the total sum of fluid delivered to the patient and the amount of time elapsed since the beginning of the IV-fluid delivery, and controls the speed with which the fluid is delivered to the patient, so that the fluid is delivered at a susbstantially constant flow rate and so that the desired amount of IV fluid is delivered in the desired length of time.

Although the invention has been described with reference to several preferred embodiments, it will be understood by one of ordinary skill in the art that various modifications can be made without departing from the spirit and the scope of the invention, as set forth in the claims hereinbelow.

What is claimed is:

1. A method for detecting the presence of a bubble in a liquid, the method comprising:

providing an acoustically resonant system having a region, the region having a first portion containing a measurement gas and a second portion containing the liquid in which the presence of the bubble is to be detected, the sum of the first portion's volume and the second portion's volume being a constant volume;

determining the resonant frequency of the system at a first pressure of the measurement gas;

changing the pressure of the measurement gas to a second pressure;

determining the resonant frequency of the system at the second pressure;

determining, based on the resonant frequency measured at the first pressure and the resonant frequency measured at the second pressure, whether the volume of the first portion has changed due to the change in pressure; and if the volumes at the first and second pressures are different, generating a signal indicating the presence of a bubble in the liquid.

2. A method according to claim 1, wherein the acoustically resonant system is tuned so as to prevent the presence of a bubble from significantly affecting a determination of the volume of the region's first portion based on the resonant frequency.

3. A method for controlling the flow of a liquid from a intravenous fluid source through an intravenous line to a patient and detecting the presence of a bubble in the liquid, the method comprising:

providing in the line a region having a first portion containing a measurement gas and a second portion containing a segment of the liquid flowing through the line, the sum of the first portion's volume and the second portion's volume being a constant volume, the region being part of an acoustically resonant system, the region being isolatable from pressure effects in the rest of the line by means of a first valve that controls flow from the source and a second valve that controls flow to the patient;

closing the second valve and opening the first valve to permit flow from the source into the region;

after liquid has flowed from the source into the region, closing the first valve so as to isolate the region from pressure effects in the line;

determining the resonant frequency of the system at a first pressure of the measurement gas;

after closing the first valve, changing the pressure of the measurement gas to a second pressure;

determining the resonant frequency of the system at the second pressure;

determining, based on the resonant frequency measured at the first pressure and the resonant frequency measured at the second pressure, whether the volume of the first portion has changed due to the change in pressure; and if no change in volume is detected due to the change in pressure, opening the second valve to permit flow to the patient, and if a change in volume is detected, generating a signal indicating the presence of a bubble in the liquid.

4. A method according to claim 3, further including the step of purging liquid from the second portion of the region to the fluid source in response to the signal indicating the presence of a bubble in the liquid.

5. A method according to claim 4, wherein the acoustically resonant system is tuned so as to prevent the presence of a bubble from significantly affecting a determination of the volume of the region's first portion based on a resonant frequency.

6. A method according to claim 4, further including the steps of determining, based on a measured resonant frequency, the volume of the measurement gas in the region's first portion before opening the second valve to permit flow to the patient;

closing the second valve after a volume of liquid has flowed to the patient;

determining the resonant frequency after the second valve is closed;

determining the first portion's volume based on the resonant frequency determined after the second valve was closed; and determining the volume of liquid delivered to the patient by subtracting the volume of the first portion determined before the second valve was opened from the volume determined after the second valve was closed.

7. A method according to claim 6, wherein the acoustically resonant system is tuned so as to prevent the presence of a bubble from significantly affecting a determination of the volume of the region's first portion based on a resonant frequency.

8. An apparatus for detecting the presence of a bubble in a liquid, the apparatus comprising:

an acoustically resonant system having a region isolated from extraneous pressure effects, the region having a first portion containing a measurement gas and a second portion containing the liquid in which the presence of the bubble to be detected, the sum of the first portion's volume and the second portion's volume being a constant volume;

means for detecting the resonant frequency of the system;

means for changing the pressure of the measurement gas in the system; and signal generating means for generating a signal indicating the presence of a bubble in the liquid, wherein the signal generating means is in communication with the means for detecting the resonant frequency and the means for changing the pressure of the measurement gas, wherein the signal is generated based upon a first and a second resonant frequency determined by the means for detecting the resonant frequency when the means for changing the pressure has caused the measurement gas to have a first and second pressure, respectively.

9. An apparatus according to claim 8, wherein the acoustically resonant system is tuned so as to prevent the presence of a bubble from significantly affecting a determination of the volume of the region's first portion based on a resonant frequency.

10. An apparatus according to claim 8, wherein the acoustically resonant system includes a back chamber, and a port containing a resonatable mass and connecting the back chamber to the first portion of the region, and wherein the resonance-detection means includes a speaker for introducing acoustic energy into the acoustically resonant system at a variety of frequencies, and a microphone for detecting the response of the acoustically resonant system to the acoustic energy introduced into the system by the speaker.

11. An apparatus according to claim 10, wherein the microphone is in communication with the back chamber and the speaker forms a portion of a wall of the back chamber.

12. An apparatus according to claim 11, wherein the resonance-detection means further includes a service chamber, in which the speaker forms a portion of the wall of the service chamber and separates the service chamber from the back chamber, and a service microphone in communication with the service chamber.

13. An apparatus according to claim 12, wherein the acoustically resonant system is tuned so as to prevent the presence of a bubble from significantly affecting a determination of the volume of the region's first portion based on a resonant frequency.

14. An apparatus for controlling the flow of a liquid from a intravenous fluid source through an intravenous line to a patient and detecting the presence of a bubble in the liquid, the apparatus comprising:

a region having a first portion containing a measurement gas and a second portion containing a segment of the liquid flowing through the line in which the presence of the bubble is to be detected, the sum of the first portion's volume and the second portion's volume being a constant volume, the region being part of an acoustically resonant system, the system having different frequencies of resonance for different volumes of the measurement gas in the first portion of the region, the region being isolatable from pressure effects in the rest of the line by means of a first valve that controls flow from the source and a second valve that controls flow to the patient;

means for detecting the resonant frequency of the system;

means for changing the pressure of the measurement gas; and a controller for controlling the valves, the resonance-detection means, and the pressure-changing means, for determining, based on the resonant frequencies measured at two different pressures, whether the volume of the first portion changes due to a change in pressure and for generating a signal indicating the presence of a bubble in the liquid if the first portion's volume does change due to a change in pressure.

15. An apparatus according to claim 14, wherein the controller causes the second valve to permit flow to the patient if no change in the first portion's volume is determined.

16. An apparatus according to claim 15, further including means for purging liquid from the second portion of the region to the fluid source in response to the signal indicating the presence of a bubble in the liquid.

17. An apparatus according to claim 16, wherein the acoustically resonant system is tuned so as to prevent the presence of a bubble from significantly affecting a determination of the volume of the region's first portion based on a resonant frequency.

18. An apparatus according to claim 17, further including means for determining the volume of the region's first portion based on a measured resonant frequency.

19. An apparatus according to claim 18, wherein the acoustically resonant system includes a back chamber, and a port containing a resonatable mass and connecting the back chamber to the first portion of the region, wherein the resonance-detection means includes a speaker for introducing acoustic energy into the acoustically resonant system at a variety of frequencies, and a microphone for detecting the response of the acoustically resonant system to the acoustic energy introduced into the system by the speaker, and wherein the microphone is in communication with the back chamber and the speaker forms a portion of a wall of the back chamber.

20. An apparatus according to claim 19, wherein the resonance-detection means further includes a service chamber, in which the speaker forms a portion of the wall of the service chamber and separates the service chamber from the back chamber, and a service microphone in communication with the service chamber.

* * * * *